(12) United States Patent
Johnsen

(10) Patent No.: US 9,962,253 B2
(45) Date of Patent: May 8, 2018

(54) LOOP VASCULAR DEVICE AND METHOD TO RETRIEVE

(71) Applicant: Cook Medical Technologies, LLC, Bloomington, IN (US)

(72) Inventor: Jeppe Dufresne Johnsen, Froerup (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 313 days.

(21) Appl. No.: 14/863,895

(22) Filed: Sep. 24, 2015

(65) Prior Publication Data

US 2016/0120634 A1 May 5, 2016

Related U.S. Application Data

(60) Provisional application No. 62/073,149, filed on Oct. 31, 2014.

(51) Int. Cl.
*A61B 17/221* (2006.01)
*A61F 2/01* (2006.01)

(52) U.S. Cl.
CPC ............ *A61F 2/01* (2013.01); *A61F 2002/011* (2013.01); *A61F 2002/016* (2013.01); *A61F 2210/0004* (2013.01); *A61F 2220/0008* (2013.01); *A61F 2250/0023* (2013.01); *A61F 2250/0031* (2013.01); *A61F 2250/0043* (2013.01); *A61F 2250/0046* (2013.01); *A61F 2250/0054* (2013.01)

(58) Field of Classification Search
CPC ............ A61B 17/221; A61B 17/32056; A61B 2017/00358; A61B 2017/2212; A61B 2017/2215; A61F 2/01; A61F 2002/011; A61F 2002/016
See application file for complete search history.

(56) References Cited

U.S. PATENT DOCUMENTS

| | | | |
|---|---|---|---|
| 5,207,686 A * | 5/1993 | Dolgin | ............. A61B 17/32056 606/1 |
| 6,620,183 B2 | 9/2003 | DiMatteo | |
| 7,867,245 B2 | 1/2011 | Neeman et al. | |
| 7,959,645 B2 | 6/2011 | WasDyke et al. | |
| 8,273,099 B2 | 9/2012 | DiMatteo | |
| 2003/0220654 A1 * | 11/2003 | Pineda | ................. A61B 17/221 606/113 |
| 2009/0254117 A1 | 10/2009 | Pakter | |
| 2010/0168758 A1 * | 7/2010 | Uihlein | ............ A61B 17/00234 606/127 |

* cited by examiner

*Primary Examiner* — Ashley Fishback
(74) *Attorney, Agent, or Firm* — Brinks Gilson & Lione

(57) ABSTRACT

The present disclosure relates to a loop vascular device and a method to retrieve said device from the body vessel of a patient. The loop vascular device comprises a loop having a first portion extending distally to a splitting portion, and a second portion also extending distally to the splitting portion, defining a close state of the loop. The splitting portion may be split such that the first portion is separated from the second portion when in the body vessel, defining an open state of the loop. In the open state, the loop may be easily retrieved through ingrowth in the body vessel, reducing or eliminating possible negative effects to the vessel wall.

20 Claims, 6 Drawing Sheets

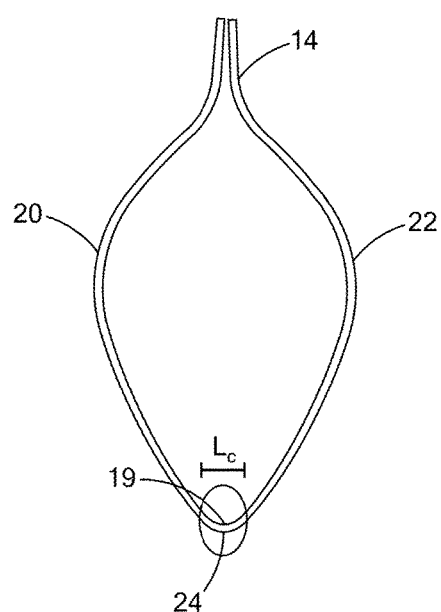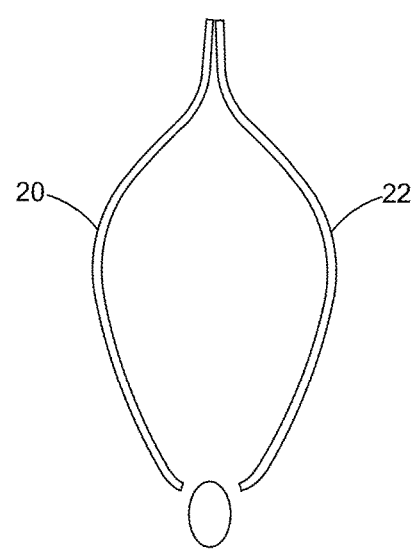
FIG. 2A                    FIG. 2B

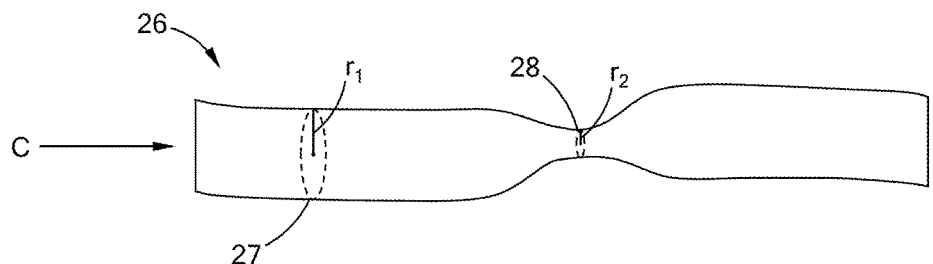
FIG. 3
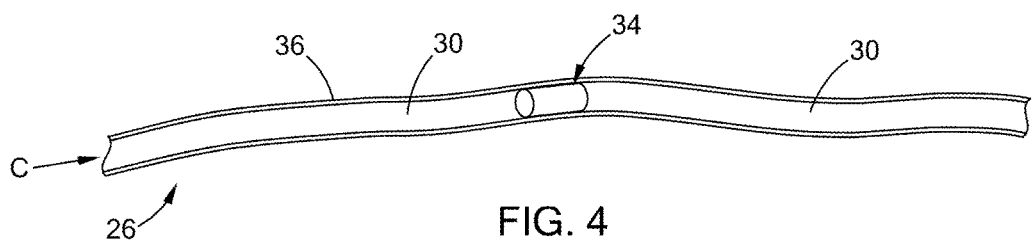
FIG. 4
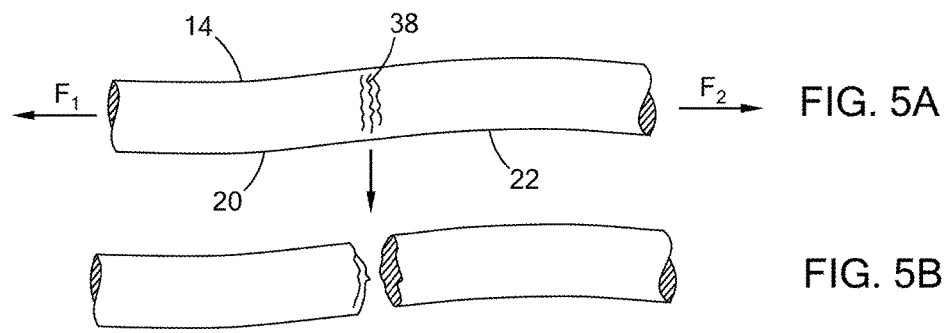
FIG. 5A
FIG. 5B
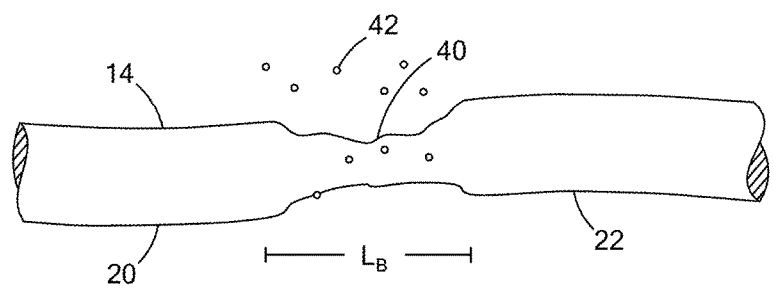
FIG. 6

LOOP VASCULAR DEVICE AND METHOD TO RETRIEVE

RELATED APPLICATIONS

This application claims the benefit of priority under 35 U.S.C. § 119(a) to U.S. Provisional Application No. 62/073,149, filed on Oct. 31, 2014, which is incorporated by reference here in its entirety.

BACKGROUND

1. Technical Field

The present disclosure relates to medical devices. More particularly, the disclosure relates to a loop vascular device and method to retrieve said device from the body of a patient.

2. Background Information

Physicians often place medical devices within the vasculature to treat conditions such as pulmonary embolism, thrombosis, and aneurysm formation. Such devices may contain closed loop portions. One advantage of such closed loops is that they may exert low force on the vessel walls. In addition, such looped portions contact the vessel walls and assist in device stabilization.

Over a period of time, device portions that contact the vessel wall may become endothelialized within the body vessel tissue. If the device is temporary, such endothelialization may make it difficult for the physician to remove these closed loop portions from the patient. There is a need for a closed loop device that is more easily retrieved after temporary placement; and a method to retrieve closed loop devices.

BRIEF SUMMARY

The present disclosure provides generally for a loop vascular device. The disclosure also provides generally for a method to retrieve said loop device. The device may comprise a loop having a first portion extending distally to a splitting portion. It further may comprise a second portion extending distally to the splitting portion. The first portion, splitting portion, and second portion define a closed state of the loop. The splitting portion may be weakened to split the first portion from the second portion when in the body vessel, defining an open state of the loop.

In one aspect, one of the first portion and the second portion has a first cross-sectional area and the splitting portion has a second cross-sectional area with the first cross-sectional area being greater than the second cross-sectional area. This difference in cross sectional area may be due to the splitting portion having a notch with the second cross-sectional area.

Likewise, the first and second portions may have a first electrical resistance and the splitting portion comprises a second electrical resistance being greater than the first electrical resistance. In this case, the device may further include an electrical insulator disposed about the loop or a portion thereof.

Relatedly, the first and second portions may comprise a first material. The splitting portion may comprise a second material being different from the first material such that the splitting portion is weakened to split the first portion from the second portion when in the body vessel, defining the open state of the loop.

The first and second materials may have an electrical wire with an electrical insulator disposed about the electrical wire. The first material may have a first electrical resistance and the second material has a second electrical resistance, the second electrical resistance may be greater than the first electrical resistance.

In yet another embodiment, the second material comprises a biodegradable portion having a biodegradable length $L_B$. Here, the loop comprises a contact portion being arranged to contact the vessel wall and having a contact length $L_C$, the contact length $L_C$ may be greater than the biodegradable length $L_B$.

Relatedly, the second material may have a mechanical weakness. The mechanical weakness may be selected from the group consisting of a brittle segment and a porous segment. In any embodiment, the splitting portion may have a length of about one (1) millimeter. Further, the device may have a plurality of loops, each loop with one splitting portion having any combination of the features discussed herein.

Said loop device has as one possible advantage that it may be easily removed if the device has been endothelialized by converting the closed loop into an open loop. The open loop has features similar to a pair of substantially straight struts. Therefore, the open loop may be fed through the endothelialized tissue reducing or eliminating any potential negative effects on the vessel wall. In one embodiment, no portion of the device remains in the body vessel after retrieval.

This disclosure further includes a method to retrieve the device as described herein. Such a method may include (1) disposing the device within the body vessel, (2) splitting the first portion from the second portion in the body vessel, and (3) retrieving the device from the body vessel. To take advantage of and/or complement the device designs, the step of splitting may include applying a current through the loop to split the first portion from the second portion. Relatedly, the step of splitting may include biodegrading a biodegradable portion.

The step of splitting may also comprise applying a first force in a first direction to the first portion and a second force in a second direction to the second portion to split the first portion from the second portion. The first and second forces may be less than 100 Newtons each. The first and second forces are about 5 Newtons to about 20 Newtons each. The first and second forces may be axial or rotational.

Additionally, the step of splitting may comprise a combination of the above disclosed steps. For example, the step of splitting may comprise two or more steps wherein the two or more steps are applying a current through the loop, biodegrading the biodegradable portion, or applying a first force in a first direction to the first portion and a second force in a second direction to the second portion to split the first portion from the second portion.

The step of retrieving may comprise retrieving through a femoral access point or a jugular access point. The step of retrieving may comprise retrieving the entire device from the body vessel.

BRIEF DESCRIPTION OF THE DRAWINGS

FIGS. 2A-B are side views of a loop of the medical device of FIGS. 1A-B;

FIG. 3 is a partial, side view of one embodiment of the loop of FIGS. 1A-B;

FIG. 4 is a partial, side view of one embodiment of the loop of FIGS. 1A-B;

FIGS. 5A-B are partial, side views of one embodiment of the loop of FIGS. 1A-B;

FIG. 6 is a partial, side view of one embodiment of the loop of FIGS. 1A-B;

DETAILED DESCRIPTION

The present disclosure provides for a loop vascular device and method to retrieve said loop device. The accompanying figures are provided for general understanding of the structure of various embodiments. However, this disclosure may be embodied in many different forms. These figures should not be construed as limiting and they are not necessarily to scale.

All publications, patent applications, patents, and other references mentioned herein are incorporated by reference in their entirety. Unless otherwise defined, all technical and scientific terms used herein have the same meaning as commonly understood by one of ordinary skill in the art to which this disclosure pertains. In case of conflict, the present document and definitions will control.

"Adjacent" referred to herein is nearby, near to, or in close proximity with.

"Axial Force" referred to herein is force applied in the direction of, on, or along an axis.

The terms "proximal" and "distal" and derivatives thereof will be understood in the frame of reference of a medical physician using the medical device. Thus, proximal refers to locations closer to the physician and distal refers to locations further away from the physician (e.g. deeper in the patient's vascular).

"Rotational Force" referred to herein is a torque or force producing rotation.

"Substantially" or derivatives thereof will be understood to mean significantly or in large part.

Figures 1A, 1B:
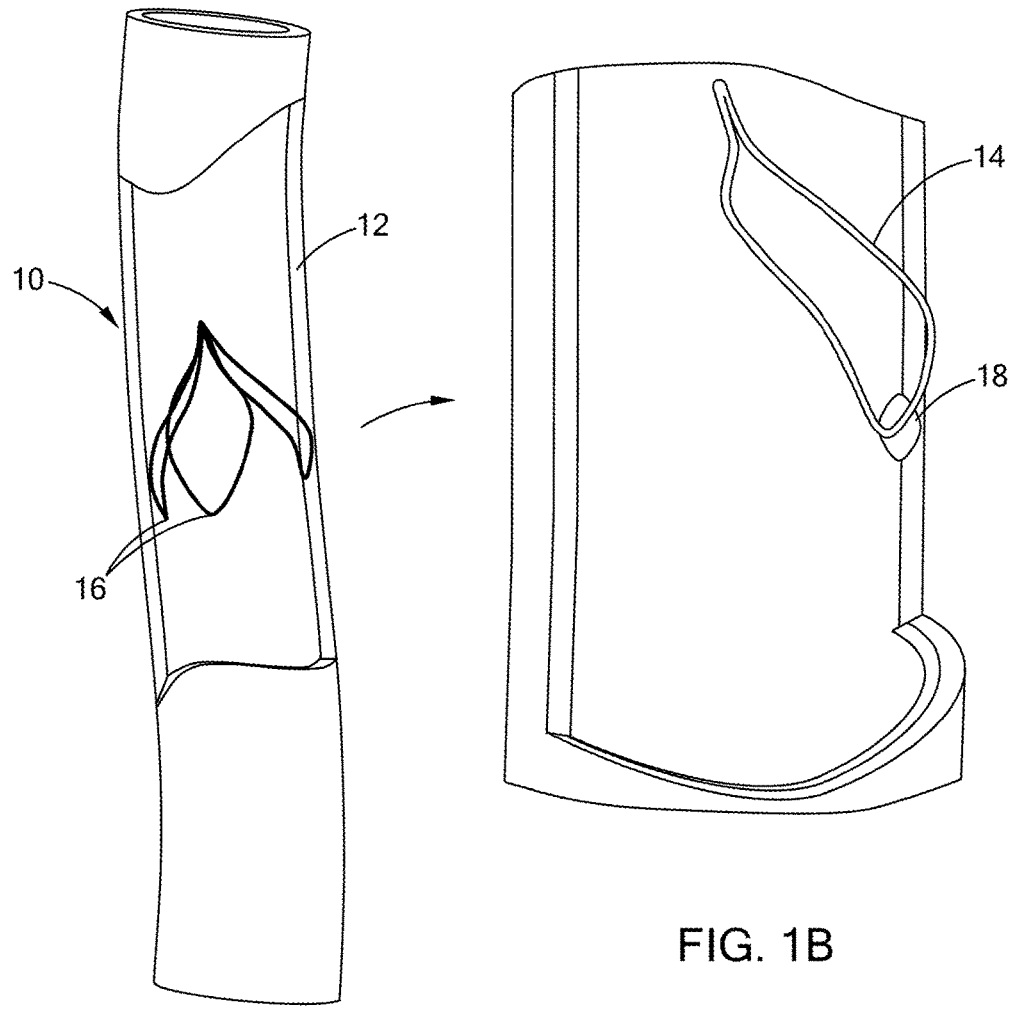
FIGS. 1A-B are environmental, side views of a medical device for treating an occlusion in a body vessel in accordance with one embodiment of the present invention.

FIGS. 1A-B illustrate loop device 10 within the body vessel. In FIG. 1A, the body vessel has vessel wall 12. The device 10 comprises loops having apices 16 contacting vessel wall 12. In a blown-up, partial view of FIG. 1A, FIG. 1B shows an isolated loop 14 of the device 10. One of skill in the art will understand that loop 14 may be representative of all loops in the device 10. Loop 14 has been ingrown or endothelialized into the vessel wall 12 with ingrowth 18. Ingrowth 18 has covered a portion of loop 14. Ingrowth 18 may assist in stabilizing device 10 within the body vessel during treatment.

After treatment, the physician may desire to remove device 10 from the body vessel. FIGS. 2A-B illustrate the closed state and the open state of loop 14, respectively, which assist in device removal after treatment. In FIG. 2A, loop 14 comprises a first portion 20 extending distally to a splitting portion 24 and a second portion 22 extending distally to the splitting portion 24, defining the closed state of loop 14.

The first portion 20 and the second portion 22 may be formed of a first material. The first and second materials may be a number of different materials, as in the different embodiments discussed herein. The splitting portion 24 comprises a second material such that the splitting portion 24 may split or weaken to split the first portion 20 from the second portion 22 when in the body vessel, defining an open state of the loop, as in FIG. 2B. Here, the first portion 20 is split from second portion 22.

Alternatively, the loop may be formed of the one material, but there may be another change, such as a change in cross-sectional area. For example, FIG. 3 illustrates one embodiment of loop being an electrical wire 26. In FIG. 3, one or both of the first and second portions may have a first cross-sectional area 27 with a radius $r_1$, and the splitting portion may have a second cross-sectional area 28 with a radius $r_2$. The first cross-sectional area 27 may be greater than the second cross-sectional area 28. For example, the splitting portion may have a notch having the second cross-sectional area 28 being easier to split upon an applied force discussed herein.

Likewise, when splitting loop 14, current may flow through the device in the direction of arrow C. Because of the possible reduced cross-sectional area at the second cross-sectional area 28, second cross-sectional area 28 may have a higher resistance to the current. Heat may build at the second cross-sectional area 28 due to this higher existence, which may cause the second cross-sectional area 28 to split or blow apart similar to a blown fuse. In this embodiment, splitting operates under Ohm's law:

$$\text{Power} = \text{Resistance} \times \text{Current}^2.$$

In this embodiment, electrical wire 26 may further be surrounded by an electrical insulator. Current flowing through the electrical wire 26 may be high enough to split the loop at the second cross-sectional area 28, but low enough not to affect the patient.

FIG. 4 illustrates another embodiment of loop 14, where there is a material change from the first and second portions to the splitting portion. Here also, the first and second materials comprise electrical wire 26. Electrical wire 26 is surrounded by electrical insulator 36 such that the electrical insulator 36 is disposed about the electrical wire 26.

In this embodiment, the first material has a first electrical resistance 30, and the second material has a second electrical resistance 34. The second electrical resistance 34 may be greater than the first electrical resistance 30 such that, when current flows through the electrical wire 26, the resistance change from the first electrical resistance 30 to the second electrical resistance 34 may cause heat build-up in the higher resistance material. As in the previously described embodiment in FIG. 3, the loop may split or blow apart to split the first portion from the second portion. The higher electrical resistance in the second electrical resistance 34 may impede the current and split the loop.

FIGS. 5A-B illustrate yet another embodiment of the loop 14. Here, loop 14 comprises a mechanical weakness 38. The mechanical weakness 38 may be selected from the group consisting of a brittle segment and a porous segment. The porous segment may create a type of reduced cross-sectional area or material difference at the splitting portion, between the first portion 20 and the second portion 22. This may predispose the splitting portion to split or break apart at the mechanical weakness 38.

Similarly, the brittle segment may create a material difference between the first and second portions and the splitting portion that predisposes the splitting portion to split based on a force applied. This force applied may be axial or rotational. In FIG. 5A, the force is an axial first force $F_1$ in a first direction and a second force $F_2$ in a second direction opposite the first direction, which splits apart the mechanical weakness 38. Through a retrieval device, the physician may introduce the first force $F_1$ in the first direction to the first portion 20 and the second force $F_2$ in the second direction to the second portion 22 to split the first portion 20 from the second portion 22.

FIG. 5B illustrates the open state of the loop after applying the axial forces. The first and second forces may be less than about 100 Newtons each. Preferably, the first and second forces are about five (5) Newtons to about twenty (20) Newtons each.

FIG. 6 illustrates a biodegradable embodiment of the device. Here, the second material comprises a biodegradable portion 40 having a biodegradable length $L_B$. After disposing the device in the body vessel, ingrowth may occur over the loop at the points where the loop contacts the vessel wall, as discussed in FIG. 2A (19). These contact points, or contact portions, have a contact length $L_C$. In one embodiment, the contact length $L_C$ is greater than the biodegradable length $L_B$.

Depending on the material chosen, after a predetermined time the biodegradable portion 40 biodegrades into biodegradable pieces 42. This biodegrading weakens and splits the splitting portion. As the biodegradable portion 40 splits, the ingrowth over the contact portion may stabilize the device. Eventually, the biodegradable portion 40 may split the first portion 20 from the second portion 22. Upon splitting, the physician may remove the device when desired.

The biodegradable material chosen for the biodegradable portion 40 may be any material known in the art, including a biodegradable polymer or metal. It will be understood that choosing a material with a shorter or longer degradation time may alter the ideal retrieval time. In addition, increasing or decreasing the amount of biodegradable material, or combining two different biodegradable materials with different degradation times, may alter the ideal retrieval time. For example, a separate coating may be applied exterior to the biodegradable portion 40 to alter the degradation time.

Further, the splitting portion may be sized for the desired device. In one embodiment, the splitting portion is about one millimeter in length. The splitting portion may be manufactured between the first and second portions through any means known in the art, including gluing, soldering, welding, or bonding the portions together. Preferably, the splitting portion may occur at or adjacent to the apex of each loop. However, the splitting portion could be positioned anywhere that the physician desires the loop to split. Depending on the number of loops, the splitting portion may be a plurality of splitting portions within each loop. Each loop may have all or some of the features described herein. In addition, each splitting portion could be formed to split at a different time from the other splitting portions.

Figure 7A:
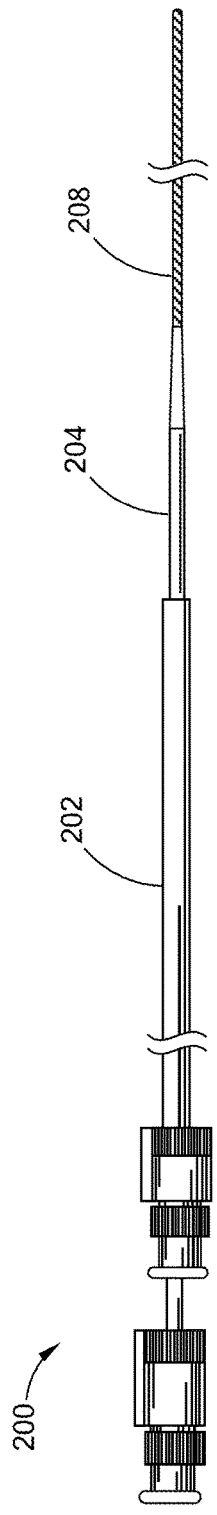
FIGS. 7A-B show a delivery assembly for the medical device of FIGS. 1A-B.

FIG. 7 illustrates a delivery or retrieval apparatus for introducing or retrieving the device discussed herein. The device may be delivered or retrieved by way of the Seldinger technique. As shown, the delivery assembly 200 includes a polytetrafluoroethylene (PTFE) introducer sheath 202 for percutaneously introducing an outer sheath 204 into a body vessel. Of course, any other suitable material for the introducer sheath 202 may be used without falling beyond the scope or spirit of the present invention.

The introducer sheath 202 may have any suitable size, for example, between about 3-FR to 8-FR. The introducer sheath 202 serves to allow the outer sheath 204 and an inner member or catheter 206 to be percutaneously inserted to a desired location in the body vessel. The inner member may also include, for example, a stylet. The introducer sheath 202 receives the outer sheath 204 and provides stability to the outer sheath 204 at a desired location of the body vessel. For example, the introducer sheath 202 is held stationary within a common visceral artery, and adds stability to the outer sheath 204, as the outer sheath 204 is advanced through the introducer sheath 202 to a treatment area in the vasculature. The outer sheath 204 has a body extending from a proximal end 216 to a distal end 210, the body being tubular and including a sheath lumen extending therethrough.

As shown, the assembly 200 may also include a wire guide 208 configured to be percutaneously inserted within the vasculature to guide the outer sheath 204 to the treatment area. The wire guide 208 provides the outer sheath 204 with a path to follow as it is advanced within the body vessel. The size of the wire guide 208 is based on the inside diameter of the outer sheath 204 and the diameter of the target body vessel.

A needle may also be used. The needle may be used for percutaneously introducing the wire guide into the patient's body through an access site. A cutting device may also be used to expand the access site.

When the distal end 210 of the outer sheath 204 is at the desired location in the body vessel, the wire guide 208 is removed and the device 10, having a proximal segment contacting a distal portion 212 of the inner catheter 206, is inserted into the outer sheath 204. The inner catheter 206 is advanced through the outer sheath 204 for deployment of the device 10 through the distal end 210 to treat the body vessel. The catheter 206 extends from a proximal portion 211 to a distal portion 212 and is configured for axial movement relative to the outer sheath 204. In this example, the distal portion 212 is shown adjacent to the device 10. Thus, before deployment, the device 10 is coaxially disposed within the lumen of the outer sheath 204 and removably coupled to the distal portion 212 of the catheter 206, or in the alternative, the device 10 is merely pushed by, but not coupled to, the distal portion 212 of the catheter 206.

The outer sheath 204 further has a proximal end 216 and a hub 218 to receive the inner catheter 206 and device 10 to be advanced therethrough. The size of the outer sheath 204 is based on the size of the body vessel in which it percutaneously inserts, and the size of the device 10.

In this embodiment, the device 10 and inner catheter 206 are coaxially advanced through the outer sheath 204, following removal of the wire guide 208, in order to position the device 10 in the body vessel. The device 10 is guided through the outer sheath 204 by the inner catheter 206, preferably from the hub 218, and exits from the distal end 210 of the outer sheath 204 at a location within the vasculature where occlusion is desired. Thus, the device 10 is deployable through the distal end 210 of the outer sheath 204 by means of axial relative movement of the catheter 206. In order to more easily deploy the device 10 into the body vessel, the device 10 may have a lubricious coating, such as silicone or a hydrophilic polymer, e.g. AQ® Hydrophilic Coating as known in the art.

Likewise, in this embodiment the device 10 may also be retrieved by positioning the distal end 210 of the outer sheath 204 adjacent the deployed device 10 in the vasculature. The inner catheter 206 is advanced through the outer sheath 204 until the distal portion 212 protrudes from the distal end 210 of the outer sheath 204. The distal portion 212 is coupled to a proximal end of the device 10, after which the inner catheter 206 is retracted proximally, drawing the device 10 into the outer sheath 204.

Figure 7B:
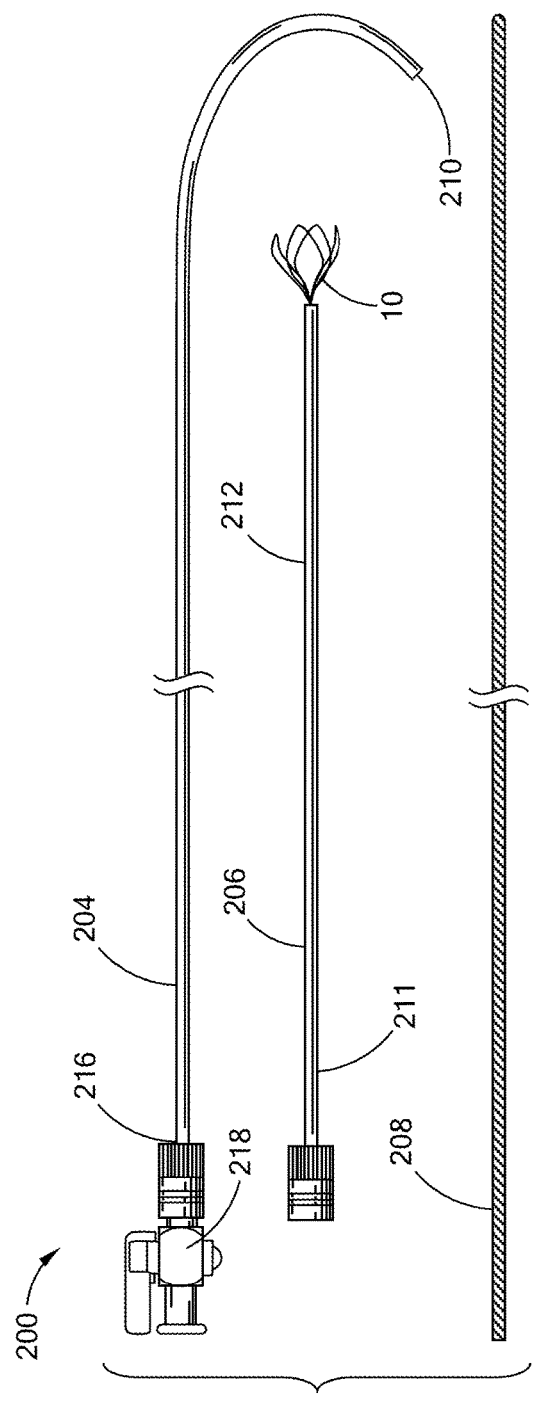

The device 10 may have a collapsed state for delivery and an expanded state for retrieval. For example, the collapsed state may have a smaller profile to fit inside the delivery apparatus. The device 10 may expand upon exiting the delivery apparatus, as shown in FIG. 7B.

Specifically, a skilled artisan will understand that the delivery or retrieval apparatus may be modified with features to perform the desired splitting technique discussed herein. For example, the distal portion 212 may be modified with electrical attachments to create the circuit for the current shown and discussed in FIGS. 3-4. In addition, the apparatus may be modified at the distal portion 212 or any other suitable location to apply the forces shown and discussed in FIGS. 5A-B. The first and second forces may either be axial applied perpendicular to the body vessel or rotationally applied to the first and second portions.

It is understood that the assembly described above is merely one example of an assembly that may be used to deploy the device in a body vessel. Of course, other apparatus, assemblies and systems may be used to deploy any embodiment of the device without falling beyond the scope or spirit of the present invention.

Figure 8:
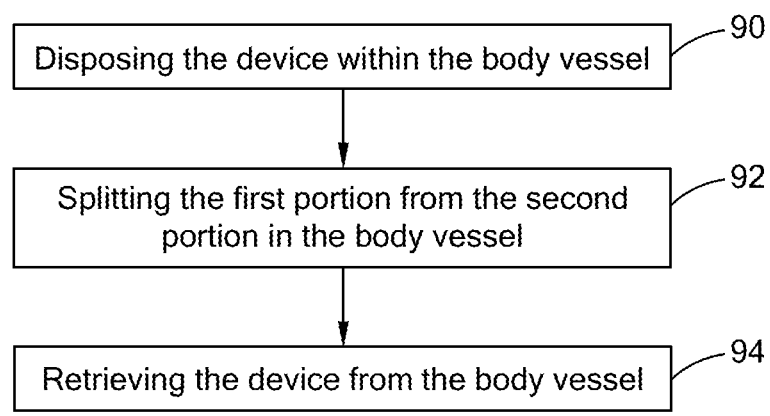
FIG. 8 is a flow diagram of one method of retrieving the medical device of FIGS. 1A-B from the body vessel in accordance with one example of the present invention.

FIG. 8 depicts a flow diagram of one method to retrieve the device discussed herein. In step 90, the physician may dispose the device within the body vessel. In step 92, the physician may split the first portion from the second portion and the body vessel using any method described herein. In step 94, the physician may retrieve the device from the body vessel.

Figure 9A:
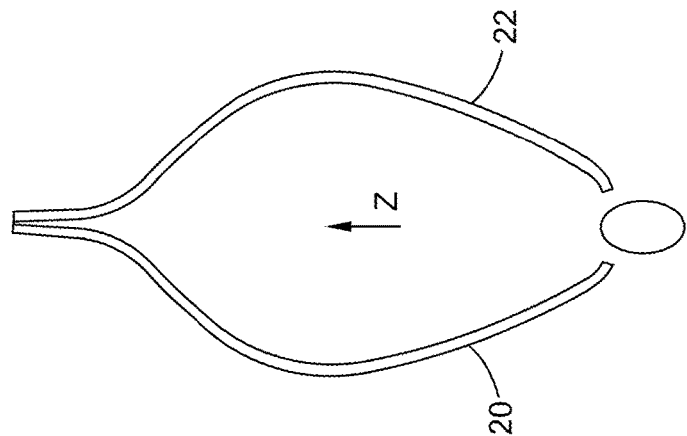
FIGS. 9A-C depict the steps of the method of FIG. 8.
Figure 9B:
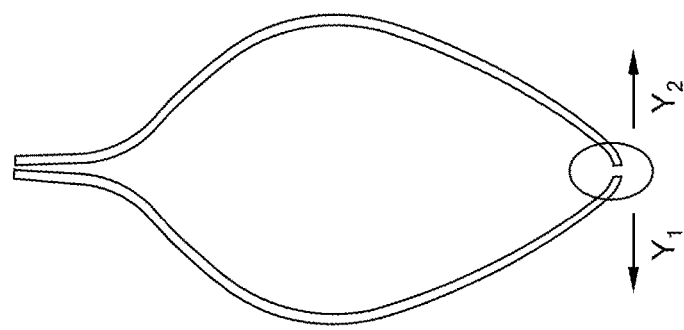
Figure 9C:
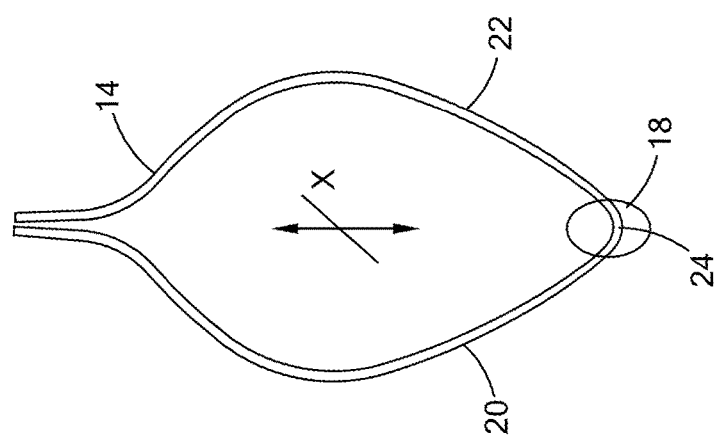

FIGS. 9A-9C depict drawings of the method steps in FIG. 8. In FIG. 9A, the loop 14 has ingrowth 18 to secure the loop 14 to the vessel wall. Because of the ingrowth 18, the loop 14 may not be able to move in the direction of arrow X. The physician may weaken the loop 14 by selecting one of the following steps. For example, the physician may weaken and split the loop by applying current through the loop 14 to split the first portion 20 from the second portion 22. Alternatively or in addition, the physician may weaken and split the loop 14 by biodegrading the biodegradable portion.

Next in FIG. 9B, the physician may split the first portion from the second portion in the direction of arrows Y1 and Y2. Alternatively, the physician may split the device by applying a first force in a first direction to the first portion and a second force in a second direction to the second portion to split the first portion from the second portion.

In either case, in FIG. 9C, the first portion 20 is split from the second portion 22. The first and second portions may form substantially straight struts, which may be retrieved or pulled through ingrowth 18 in the direction of arrow Z, reducing or eliminating possible negative effects upon retrieval.

In another embodiment, splitting the first portion from the second portion may involve a combination of the steps described herein. For example, splitting may comprise biodegrading a biodegradable portion and then applying a first force in a first direction to the first portion and a second force in a second direction to the second portion. The step of splitting may comprise two or more steps wherein the two or more steps are applying a current through the loop, biodegrading the biodegradable portion, or applying a first force in a first direction to the first portion and a second force in a second direction to the second portion to split the first portion from the second portion.

The step of retrieving may further comprise retrieving through a femoral access point or a jugular access point. A skilled artisan will understand that a physician may use either a femoral access point or a jugular access point to perform the Seldinger technique. In addition, the step of retrieving may comprise retrieving the entire device from the body vessel such that no part of the device remains in the body vessel after retrieval. All parts of the device may be removed by either femoral or jugular access.

While the present invention has been described in terms of certain preferred embodiments, it will be understood that the invention is not limited to these disclosed embodiments as those having skill in the art may make various modifications without departing from the scope of the following claims.

The invention claimed is:

1. A device for treatment in a body vessel, the body vessel having a vessel wall, the device comprising:
a loop comprising a first portion extending distally to a splitting portion and a second portion extending distally to the splitting portion, defining a closed state of the loop, wherein the first and second portions comprise a first electrical resistance and the splitting portion comprises a second electrical resistance being greater than the first electrical resistance, such that current flows through the device, causing the splitting portion to split or blow apart when in the body vessel, defining an open state of the loop.

2. The device of claim 1 wherein one of the first portion and the second portion has a first cross-sectional area and the splitting portion has a second cross-sectional area, the first cross-sectional area being greater than the second cross-sectional area.

3. The device of claim 2 wherein the splitting portion comprises a notch having the second cross-sectional area.

4. The device of claim 1 wherein the device further comprises an electrical insulator disposed about the loop.

5. The device of claim 1 wherein the loop is a plurality of loops, each loop comprising one splitting portion.

6. A device for treatment in a body vessel, the body vessel having a vessel wall, the device comprising:
a loop comprising a first portion extending distally to a splitting portion and a second portion extending distally to the splitting portion, defining a closed state of the loop,
wherein the first and second portions comprise first material, and the splitting portion comprises a second material being different from the first material such that the splitting portion is weakened to split the first portion from the second portion when in the body vessel, defining an open state of the loop.

7. The device of claim 6 wherein the first material and the second material comprise an electrical wire, the device further comprising an electrical insulator disposed about the electrical wire.

8. The device of claim 6 wherein the first material has a first electrical resistance and the second material has a second electrical resistance, the second electrical resistance being greater than the first electrical resistance.

9. The device of claim 6 wherein the second material comprises a biodegradable portion having a biodegradable length $L_B$ and the loop comprises a contact portion having a contact length $L_C$ to contact the vessel wall, the contact length $L_C$ being greater than the biodegradable length $L_B$.

10. The device of claim 6 wherein the second material comprises a mechanical weakness.

11. The device of claim 10 wherein the mechanical weakness is selected from the group consisting of a brittle segment and a porous segment.

12. The device of claim 6 wherein the loop is a plurality of loops, each loop comprising one splitting portion.

13. A method for retrieving a device from a body vessel, the body vessel having a vessel wall, the method comprising:

disposing the device within the body vessel, the device comprising:
- a loop comprising a first portion extending distally to a splitting portion and a second portion extending distally to the splitting portion, defining a closed state of the loop, wherein the first and second portions comprise a first material, and the splitting portion comprises a second material being different from the first material such that the splitting portion is weakened to split the first portion from the second portion when in the body vessel, defining an open state of the loop;
- splitting the first portion from the second portion in the body vessel; and
- retrieving the device from the body vessel.

14. The method of claim 13 wherein the step of splitting comprises applying a current through the loop to split the first portion from the second portion.

15. The method of claim 13 wherein the step of splitting comprises applying a first force in a first direction to the first portion and a second force in a second direction to the second portion to split the first portion from the second portion.

16. The method of claim 15 wherein the step of applying the first and second forces comprises the first and second forces being less than 100 Newtons each.

17. The method of claim 15 wherein the step of applying the first and second forces comprises the first and second forces both being axial or rotational.

18. The method of claim 13 wherein the step of splitting comprises biodegrading a biodegradable portion.

19. The method of claim 13 wherein the step of splitting comprises two steps selected from the group consisting of applying a current through the loop, biodegrading a biodegradable portion, and applying a first force in a first direction to the first portion and a second force in a second direction to the second portion to split the first portion from the second portion.

20. The method of claim 13 wherein the step of retrieving comprises retrieving the entire device from the body vessel.

* * * * *